(12) United States Patent
Shahidi et al.

(10) Patent No.: US 6,442,417 B1
(45) Date of Patent: Aug. 27, 2002

(54) METHOD AND APPARATUS FOR TRANSFORMING VIEW ORIENTATIONS IN IMAGE-GUIDED SURGERY

(75) Inventors: Ramin Shahidi, San Francisco; Rory S. Randall, San Diego; Steven L. Datnow, San Jose, all of CA (US)

(73) Assignees: The Board of Trustees of the Leland Stanford Junior University, Stanford, CA (US); CBYON, Inc., Palo Alto, CA (US)

(*) Notice: Subject to any disclaimer, the term of this patent is extended or adjusted under 35 U.S.C. 154(b) by 94 days.

(21) Appl. No.: 09/723,819

(22) Filed: Nov. 28, 2000

Related U.S. Application Data
(60) Provisional application No. 60/167,939, filed on Nov. 29, 1999.

(51) Int. Cl.[7] .................................................. A61B 5/05
(52) U.S. Cl. ......................... 600/429; 600/117; 606/130
(58) Field of Search ................................... 600/427, 429, 600/426, 411, 417, 424, 407, 117; 606/130

(56) References Cited

U.S. PATENT DOCUMENTS

| | | | | |
|---|---|---|---|---|
| 6,167,296 A | * | 12/2000 | Shahidi | 600/427 |
| 6,246,898 B1 | * | 6/2001 | Vesely et al. | 600/424 |
| 6,374,135 B1 | * | 4/2002 | Bucholz | 600/427 |

* cited by examiner

*Primary Examiner*—Peter Nerbun
(74) *Attorney, Agent, or Firm*—Perkins Coie LLP

(57) ABSTRACT

Systems and methods for performing transformations between a view orientation in a virtual space and a view orientation with respect to a target site in a patient's body where surgery is being performed. The view in virtual space enables the surgeon to see the internal structures in the target site in a variety of ways and orientations including from behind the site.

33 Claims, 9 Drawing Sheets

METHOD AND APPARATUS FOR TRANSFORMING VIEW ORIENTATIONS IN IMAGE-GUIDED SURGERY

This application claims priority to U.S. provisional application having serial No. 60/167,939 filed on Nov. 29, 1999, which is hereby incorporated by reference in its entirety.

FIELD OF THE INVENTION

The present invention relates to systems, devices and methods for transforming between a view orientation with respect to a virtual point external to a patient or with respect to an axis along which the virtual point is viewed and a view orientation with respect to a target point or with respect to an axis along which the target point is viewed for navigation purposes. The invention also relates to a device-readable medium embodying a program of instructions (i.e., software) for implementing the transformation method(s).

BACKGROUND OF THE INVENTION

Image-guided surgery generally involves: (1) acquiring 2-D images, either preoperatively or intraoperatively, of internal anatomical structures of interest, e.g., of a patient target site; (2) reformating a 2-D image or reconstructing a 3-D image based on the acquired 2-D images; (3) segmenting the images; (4) registering the patient to the images; (4) targeting a site of interest in the patient; and (5) navigating to that point.

Typically, the acquired 2-D images are reformatted to generate two additional sets of 2-D images. One of the sets of images is parallel to a first plane defined by two of the three axes in a 3-D coordinate system, say, the xy-plane; a second set is parallel to, say, the xz-plane; and a third set is parallel to, say, the yz-plane.

Registration between the patient and the image provides a basis by which a medical instrument, such as an endoscope, can be tracked in the images as it is moved within the operating field during surgery.

Registration is the point-for-point mapping of one space to another allowing corresponding points to be mapped together. Corresponding points are those points that represent the same anatomical features in two spaces. There are multiple registration algorithms, such as fiducial based, intensity based and entropy based, that can be used to register two spaces, such as image-to-image and image-to-physical. For example, a fiducial based, image-to-physical algorithm uses as input the 3-D positions of three or more fiducial markers in both spaces, and outputs the point-for-point mapping from one space to another. The mapping addresses the physical differences in position of the two spaces, which consists of a shift, rotation, scale or any combination thereof. The correct mapping, or registration, is the particular rotation, shift or scale that will map all the localized fiducial positions in one 3-D space, for example, the physical space around the patient in the operating room, to the corresponding localized positions in the second space, for example, a CT image. If these fiducial positions are properly mapped then, unless there is distortion in the images, all non-fiducial points in the first space will be mapped to corresponding points in the second space as well. These non-fiducial points are the anatomical points of interest to the surgeon. Because of inevitable small errors in the localization of the fiducial points, it is rarely possible to find a rotation, shift or scale that will map all fiducial points exactly from one space to the other. Therefore, an algorithm is used that finds the rotation, shift or scale that will produce the smallest fiducial mapping error (in the standard least-squares sense). This mapping error provides a measure of the success of the registration. It is computed by first calculating, for each fiducial point the distance between its localized position in the second space and the localized position in the first space as mapped into the second space. The mapping error is then computed by calculating the square root of the average of the squares of these distances.

With registration established, the endoscope can be tracked relative to the internal structures of the patient as it is navigated in and around the patient target site during surgery. Images of the target site are displayed to assist the user (e.g., surgeon) in navigating to the target site. Current methods of tracking include the use of robotic or mechanical arms, or optical, sonic or magnetic devices. Tracking may be based on, for example, the known mathematics of "triangulation."

Further details regarding techniques involved in image-guided surgery are disclosed in g U.S. application Ser. No. 08/884,289, entitled "Method and Apparatus for Volumetric Image Navigation," filed Jun. 27, 1997, now abandoned and international application, publication no.: WO 99/00052, publication date: Jan. 7, 1999. U.S. application Ser. No. 09/411,363, filed Sept. 30, 1999, now U.S. Pat. No. 6,167, 296 is a continuation of U.S. application Ser. No. 08/884, 209. The contents of each of these applications are incorporated herein by reference.

One of the problems with conventional navigation systems is that usually the endoscope has a limited range of movement once inside the patient. This, in turn, limits the view orientations with which the target site may be viewed. For example, it is usually not possible to move the endoscope even 20° one way or the other with respect to a point in the target site to obtain views from those perspectives, and it is almost never possible to move the endoscope 180° to view the target site from the other side. This significantly limits the information available to the surgeon.

SUMMARY OF THE INVENTION

The present invention overcomes this problem by providing systems and methods for obtaining view information of a patient target site that is independent of the range of movement of a medical instrument, such as an endoscope.

In one aspect of the invention, an apparatus is provided for use in an image-guided surgical or a diagnostic procedure at an internal target site of a patient. The apparatus comprises:

(a) a data-storage medium for storing scan data representing internal scans of the patient target site;

(b) an instrument defining a view axis, where the instrument is adapted to be moved to a selected orientation with respect to the patient target site;

(c) means for tracking the orientation of the instrument with respect to the patient target site as the instrument is moved;

(d) a display device; and (e) a processor in communication with the data storage medium, the tracking means, and the display device, for carrying out steps (i)–(iii) in a first mode of operation, and steps (iv)–(viii) in a second mode of operation.

The first mode of operation includes: (i) determining the orientation of the instrument view axis with respect to the patient target site, as the instrument is moved to a selected orientation with respect to the patient target site; (ii) using at least some of the scan data to construct an image of the patient target site, as viewed with respect to the orientation of the instrument; and (iii) displaying the image on the display device.

The second mode of operation includes: (iv) receiving input that indicates a selected orientation at which a virtual target point, external to the patient, is being viewed; (v) determining, from the input, the selected view orientation with respect to the virtual target point; (vi) transforming the view orientation determined in step (v) to a view orientation with respect to the selected patient target point; (vii) using the scan data to construct an image of the patient target site, as viewed along the transformed view orientation generated in step (vi); and (viii) displaying the image generated in step (vii) on the display device.

DETAILED DESCRIPTION OF THE INVENTION

Figure 1:
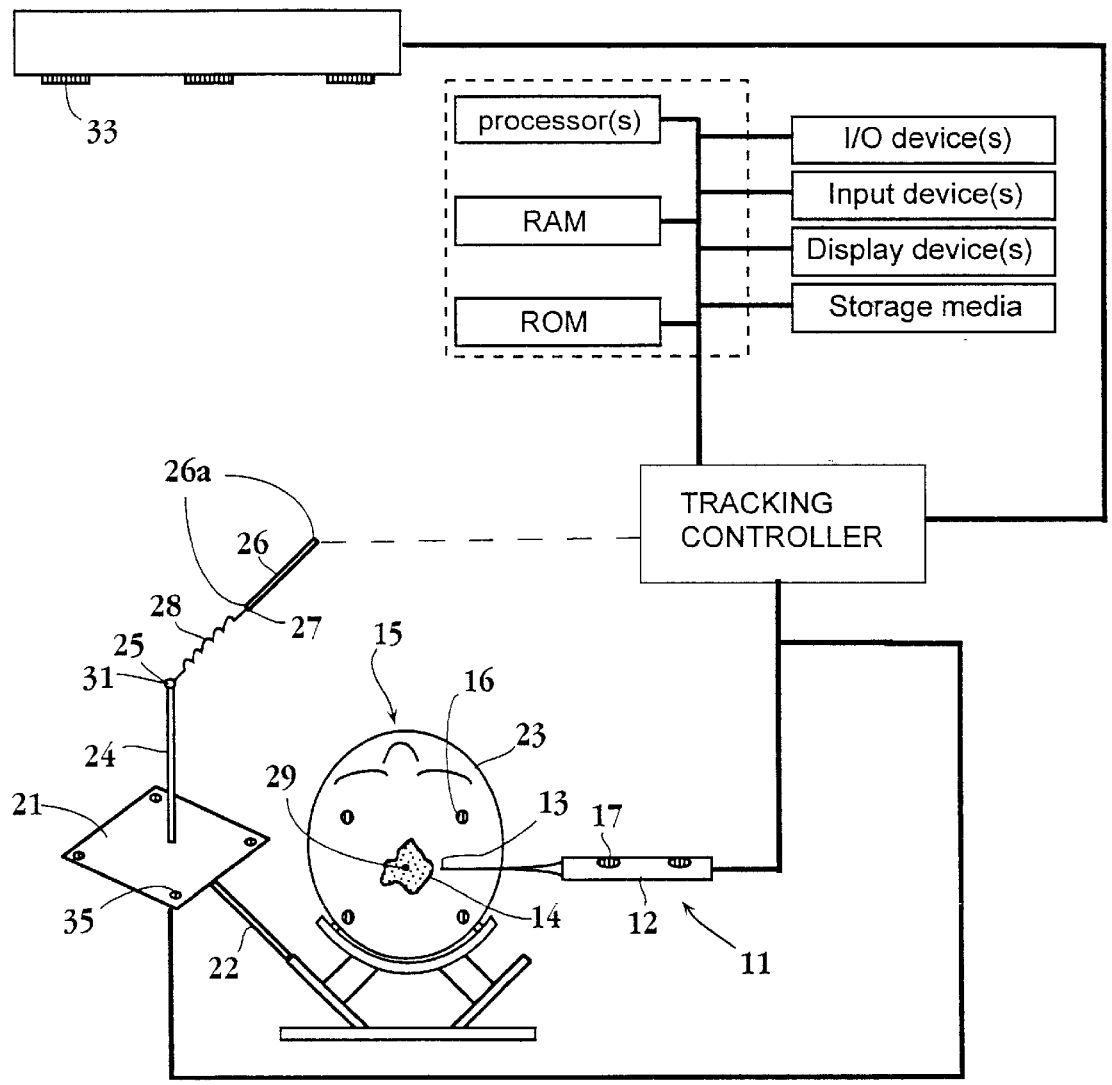
FIG. 1 is a partially perspective partially schematic view of an image-guided surgery system with which the present invention may be employed.

FIG. 1 illustrates an image-guided surgery system with which the present invention may be employed. The system includes a surgical or medical instrument 11, such as an endoscope, having an elongate axis 12 and tip 13, which is used to probe an internal target site 14 of a patient 15. A plurality of fiducials or markers 16 are placed on the patient 15 near the target site. The fiducials are used to register corresponding points on the preoperative or intraoperative 2-D image scans of patient target site 14. Instrument 11 has a plurality of tracking elements 17 on its shaft 12 which emit signals to sensors 33 positioned in view of the instrument. Both the instrument and the sensors are in communication with a tracking controller which is in communication with a computer system that processes the signals received by sensors 33 to track the movement of instrument 11 during surgery. The tracking controller may be a separate element or it may be physically integrated with the computer system and may even be embodied in an option card which is inserted into an available card slot in the computer. The computer system is also used to render and display the 2-D preoperative or intraoperative images and render 3-D surface or volumetric images, either of which may be perspective or orthographic, of target site 14 on a display device.

Various aspects of the image-guided surgery procedure, such as registration, tracking, image generation and navigation, may be implemented by a program of instructions (e.g., software) in response to user input supplied by various input devices such as a keyboard, mouse, track ball or joystick. The software is executed by a processor, such as a central processing unit (CPU) which may be in the form of a microprocessor. Other processors may also be used in conjunction with the CPU such as a graphics chip.

As shown in FIG. 1, a dynamic frame-of-reference (DFR) 21 is rigidly attached to a support 22 that is securely attached to the portion of patient 15 (e.g., head 23) where the surgery is to be performed. Thus, when the patient's head moves, support 22 and DFR 21 also move. Securely attached to the DFR is a rigid elongated element 24 extending outwardly from a main surface of DFR 21 at a known angle and terminating in a tip 25 at its distal end. DFR 21 includes a plurality of sensors 35 in communication with tracking controller which is also in communication with the computer system, instrument 11 and sensors 33 to determine the location and orientation of the DFR including element 24 and its tip 25. In accordance with one variation of the preferred embodiment of the invention, a pointer 26 has its tip 27 attached to one end of an elastic, telescopic or otherwise length-adjustable potentiometer 28 or equivalent device, the other end of which is attached to tip 25. If pointer 26 is not attached to DFR 21, then the pointer will include tracking elements/position sensors 26a that are in communication with sensors 33 and the computer system to track the movement and determine the position and orientation of the pointer.

The remaining figures. taken in conjunction with FIG. 1 describe the various embodiments of the invention.

Figure 2:
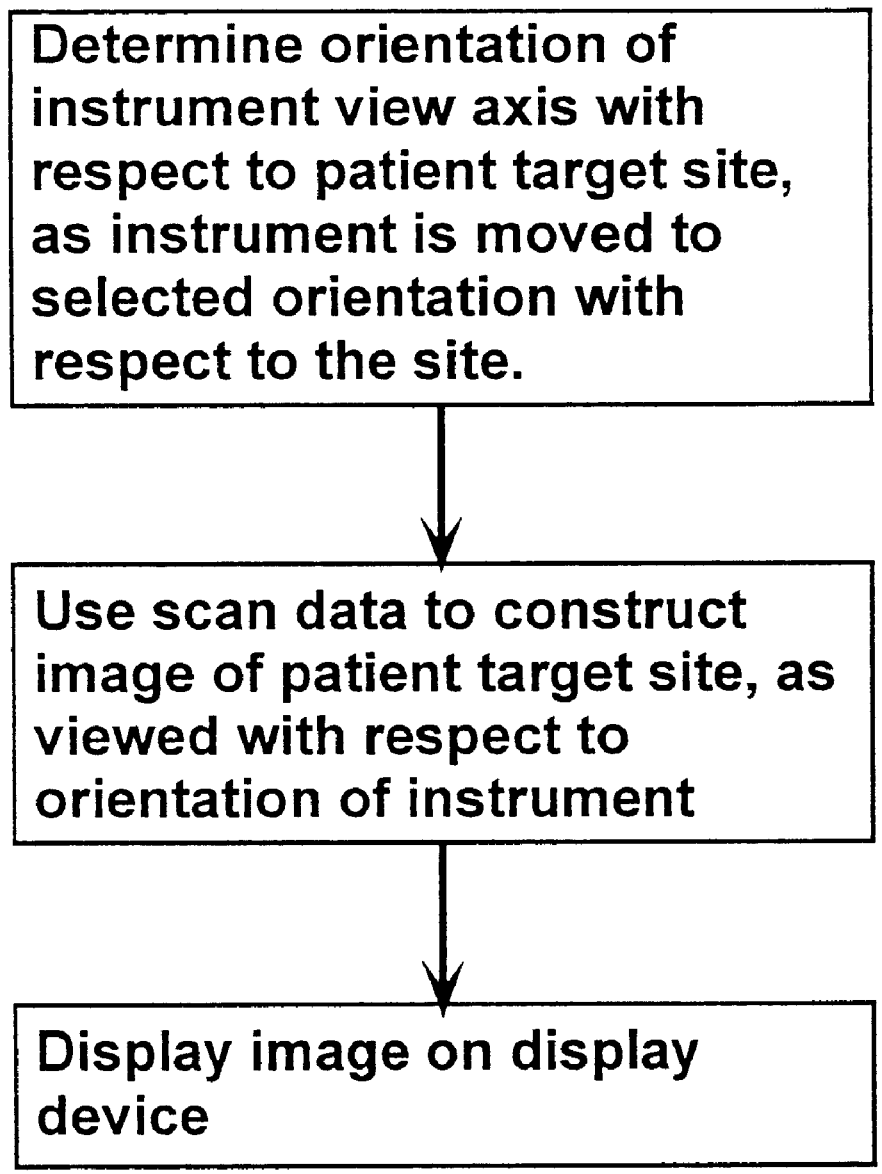
FIG. 2 is a flow chart illustrating a first mode of operation in accordance with the present invention.

FIG. 2 illustrates a first mode of operation in accordance with embodiments of the invention. First, the user selects a target point 29 in patient target site 14 and establishes the orientation of the instrument view axis (e.g., the endoscope view axis) with respect to target point 29. Next, selected preoperative or intraoperative scan data representing internal scans of the patient target site are used to construct an image of the patient target site, with respect to the orientation of the instrument, such as viewed along the view axis of the instrument. That is, the constructed image is orthogonal to the view axis of the instrument but is viewed along the axis of the instrument. The image is then displayed in various 2-D orientations and in 3-D on the display device for viewing by the user.

Figure 3:
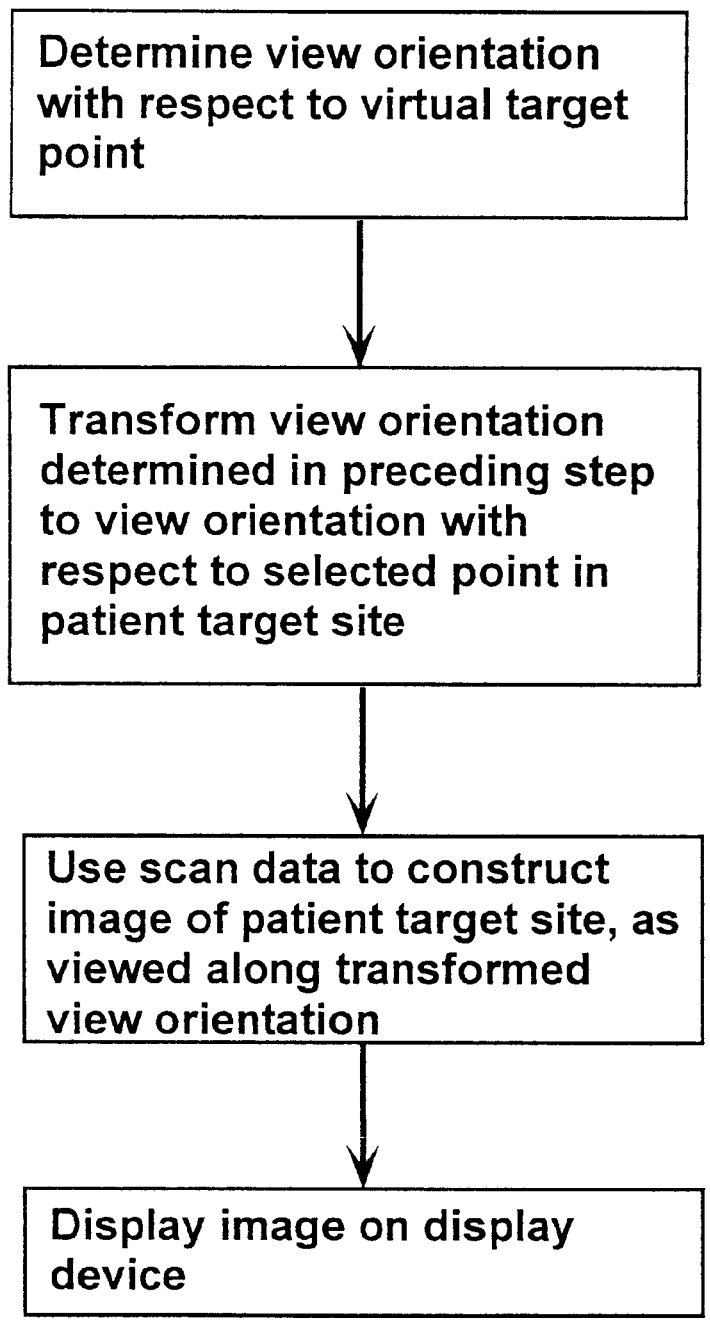
FIG. 3 is a flow chart generally illustrating a second mode of operation in carrying out the view orientation transformation methods of the present invention.

FIG. 3 illustrates a second mode of operation, in accordance with embodiments of the invention, where a view orientation with respect to a virtual target point 31, external to the patient, is transformed to a view orientation with respect to a selected target point 29 in the patient. The virtual target point may be established at any external location that can be determined relative to the tracking system, e.g., relative to DFR 21. For example, virtual target point 31 can be at the tip of elongated support 24 as shown in FIG. 1, or it can be located in free space and initially defined by the tip of pointer 26.

As illustrated in FIG. 3, the user selects an orientation with which to view the virtual target point and the corresponding image of patient target site 14. The view orientation of the virtual target point is defined by an imaginary line extending between a known point on the pointer, e.g., its tip 27 and virtual target point 31. Thus, selecting the view orientation also involves selecting the location of the virtual target point, if it is not at a fixed location, e.g., at the tip of the elongated support, as shown in FIG. 1. The virtual target point can be defined in free space by moving the tip of the pointer to the desired point in space and clicking a selector button on pointer 26 to establish virtual target 31 point at the tip of the pointer. The virtual target point will remain at that location even after the pointer is moved, until a new virtual target point is established by the user.

The selected view orientation and virtual target point location is then input into the computer where this information is processed and stored. In particular, the computer establishes a correspondence between selected target point 29 in patient target site 14 and virtual target point 31 in "virtual" space, which may be accomplished, for example, using point-to-point mapping. Point-to-point mapping essentially involves determining a transformation matrix that maps the coordinates of point 29 to another set of coordinates representing point 31. A transformation is then made between the view orientation with respect to virtual target point 31 and the view orientation with respect to selected point 29. Scan data is used to construct an image of the patient target site, as viewed along the view orientation with respect to the virtual target point. The image is then displayed on the display device.

Figure 4:
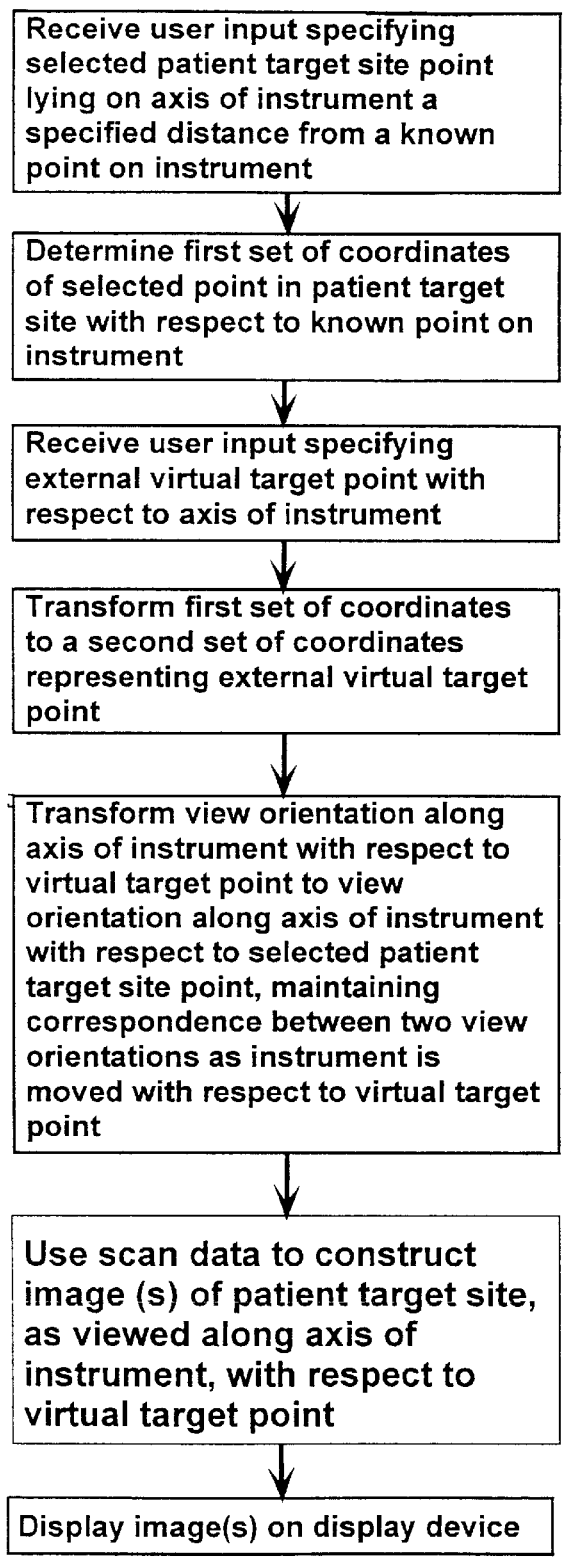
FIG. 4 is a flow chart illustrating a view orientation transformation in accordance with a first embodiment of the present invention.
Figure 5:
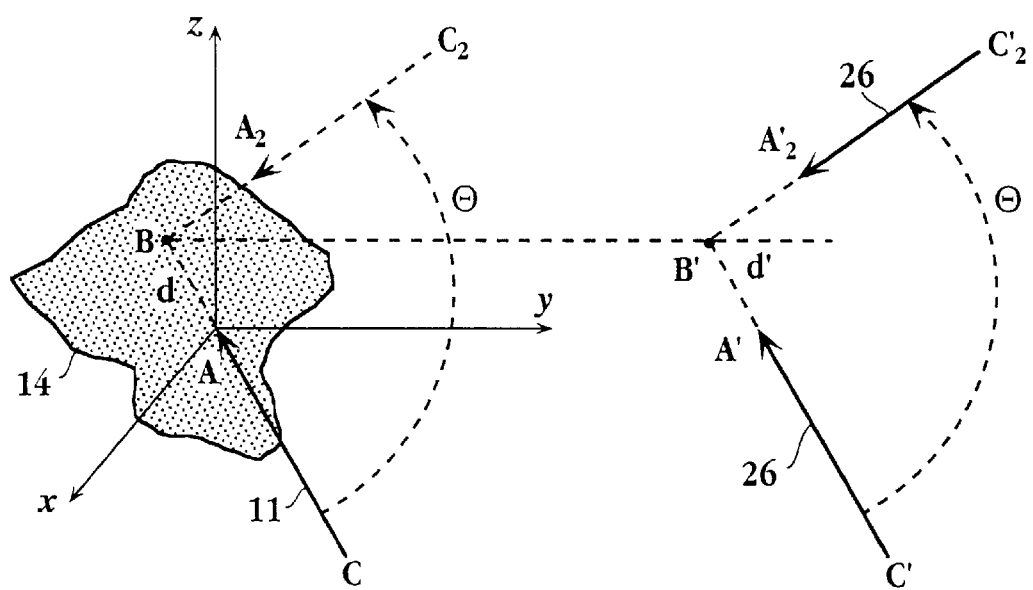
FIG. 5 is a schematic diagram illustrating the view transformation in accordance with the first embodiment of the present invention.

FIGS. 4 and 5 illustrate a preferred embodiment of the second mode of operation, where the virtual target point is located a specified distance from a known point on the pointer 26 which is used to view the virtual target point and the corresponding image of the patient target site 14 along the axis of the pointer 26. It should be noted that in this embodiment as well as in the other disclosed embodiments pointer 26 may be the medical instrument used at the patient target site 14 or it may be a separate instrument.

The user selects a target point B in the patient target site 14 that lies on the axis of the instrument 11 at a selected distance d from a known point A on the instrument 11 and inputs this information into the computer. The coordinates $x_1$, $y_1$, $z_1$ of selected point B in the patient target site are determined with respect to known point A.

Next, the user specifies an external virtual target point B' with respect to the axis of pointer 26. This may be accomplished, for example, by clicking a selector button on pointer 26 to establish B' at the tip of the pointer relative to its axis. The coordinates $x_1$, $y_1$, $z_1$ of B are transformed to a second set of coordinates $x_1'$, $y_1'$, $z_1'$ representing B' to establish correspondence between points B and B' in their respective spaces.

A transformation is then made between the view orientation along the axis of pointer 26 with respect to point B' at distance d' and the view orientation along the axis of instrument 11 with respect to point B at distance d, where d and d' may or may not be equal. These transformations establish correspondence between the two view orientations, so that the view that the user sees along the axis of pointer 26 at distance d' is the same view as the user sees (or would see) along the axis of instrument 11 at distance d in the corresponding view orientation. Now, as pointer 26 is moved, say, counterclockwise through an angle θ to the position shown in FIG. 5, the user now sees patient target site 14 through point B' as if instrument 11 was moved that same angular distance to the position shown in a dashed line in FIG. 5. Also, if the user were to move pointer 26 along its axis, say away from B' thereby increasing d', the user would view target site 14 as if instrument 11 was also moved along its axis away from B to increase d. The computer may maintain a constant ratio between d and d', or alternatively may employ other linear or nonlinear mathematical relationships between d and d' in correlating the view distances.

Scan data is used to construct images of the patient target site 14, as viewed along the axis of the pointer 26, with respect to B', and these images are displayed on the display device.

A variation on the above-described embodiment is to use a "universal swivel" device connecting the tip of elongated element 24 (which in this case represents virtual target point B') to the tip of the pointer 26 (point A'in FIG. 5). The universal swivel device may be potentiometer 28 or equivalent device. Here, point B' is at a known location and d' may easily be determined using the potentiometer 28. Preferably, the potentiometer is adjustable along its axis to allow the pointer to be moved in and out but keeps the axis of the pointer aligned with the axis of the potentiometer. Thus, this arrangement enables pointer 26 to rotate about virtual point B' while maintaining co-linearity between any two points on the pointer 26 and B'.

The "universal swivel" may also be implemented using a joystick, or similar device. Here the ball of the joystick represents virtual target point B' and the joystick itself represents pointer 26. View distance d' is fixed and corresponds to some view distance d in the patient target site. The joystick need not be tracked using sensors but would interface with the computer as an input device so that its position can be determined. The user inputs information to the computer to establish distance d', a reference view orientation with respect to point B', and a corresponding reference joystick position. Based on that information, the computer then employs an algorithm to correlate different positions of the joystick with different view orientations with respect to point B', which, in turn, is correlated with various view orientations of instrument 11 with respect to target point B. As the joystick is moved, the view orientation that the user sees on the display device changes.

The "universal swivel" may also be implemented using a track ball as a computer input device. Once calibrated, manipulating the track ball can be used to change the view orientation vector A'B' which is correlated to various view orientations of instrument 11 represented by vector AB. Here there is no pointer 26, and the view orientation with respect to B' is relative to the position of the track ball. As with the joystick, view distance d' is fixed and corresponds to a view distance d in the patient target site. The user inputs information to the computer to establish d' which is correlated with d.

Figure 6:
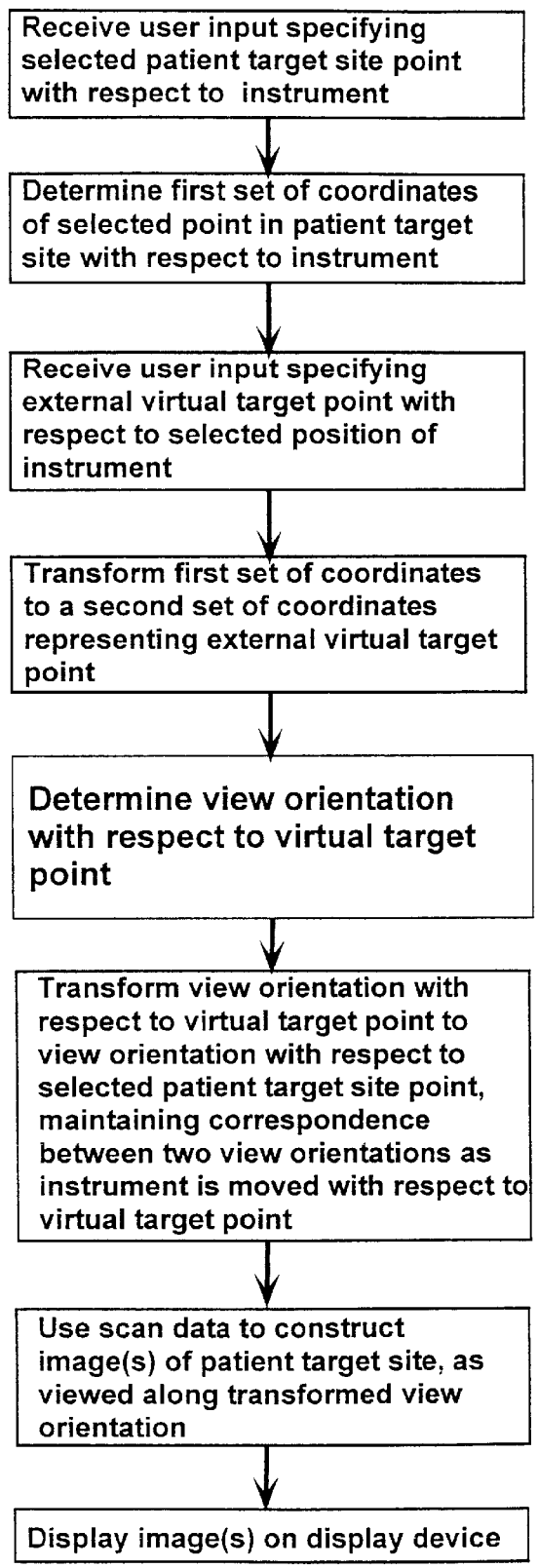
FIG. 6 is a flow chart illustrating a view orientation transformation in accordance with a second embodiment of the present invention.
Figure 7:
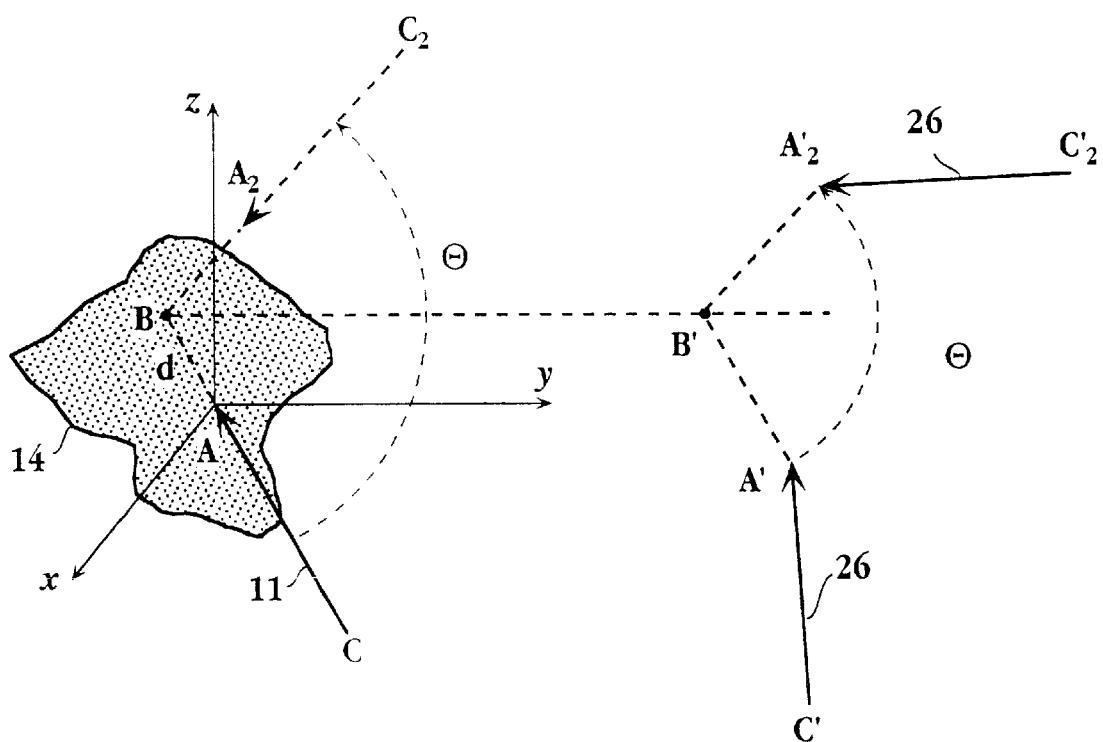
FIG. 7 is a schematic diagram illustrating the view transformation in accordance with the second embodiment of the present invention.

In another embodiment of the second mode of operation, which is more general than the first embodiment, a transformation is made between a view orientation with respect to a selected virtual target point and a view orientation with respect a selected patient target site point, where the view orientations may or may not be along the axis of the instrument/pointer. An example of this embodiment is illustrated in FIGS. 6 and 7, where the view orientation with respect to the target point is along the axis of the instrument but the view orientation with respect to the virtual target point is not along the axis of the pointer. This is merely one example of this embodiment; other variations are possible.

Referring now specifically to FIGS. 6 and 7, the user supplies input specifying a target point B in patient target site 14, where B is defined relative to the instrument, e.g., B lies along the axis of the instrument 11. The coordinates $x_1$, $y_1$, $z_1$ of selected point B in the patient target site are determined with respect to the position of the instrument. The coordinates $x_1$, $y_1$, $z_1$ and a distance d may be determined relative to a known point, say A, on the tip of instrument 11. The imaginary line between B and A defines the view orientation with respect to the selected patient target site point.

Next, the user specifies an external virtual target point B' with respect to the position of pointer 26. This may be accomplished, for example, by using a position selector on the pointer as previously described. The coordinates $x_1$, $y_1$, $z_1$ are transformed to a second set of coordinates $x_1'$, $y_1'$, $z_1'$ representing B', and the view orientation in the "virtual" space is determined by the line between A' and B'.

A transformation is then made between the view orientation defined by vector A'B' and the view orientation defined by vector AB. Thus, as the tip of pointer 26 is moved, say, counterclockwise through an angle θ, as shown in FIG. 7, the user now sees patient target site 14 as if instrument 11 were moved that same angular distance to the position shown in dashed lines in FIG. 7. That is, view orientation $A'_2B'$ in the "virtual" space corresponds to view orientation $A_2B$ in the "real" space.

Scan data is used to construct images of the patient target site 14, as viewed along the transformed view orientation, and these images are displayed on the display device.

Figure 8:
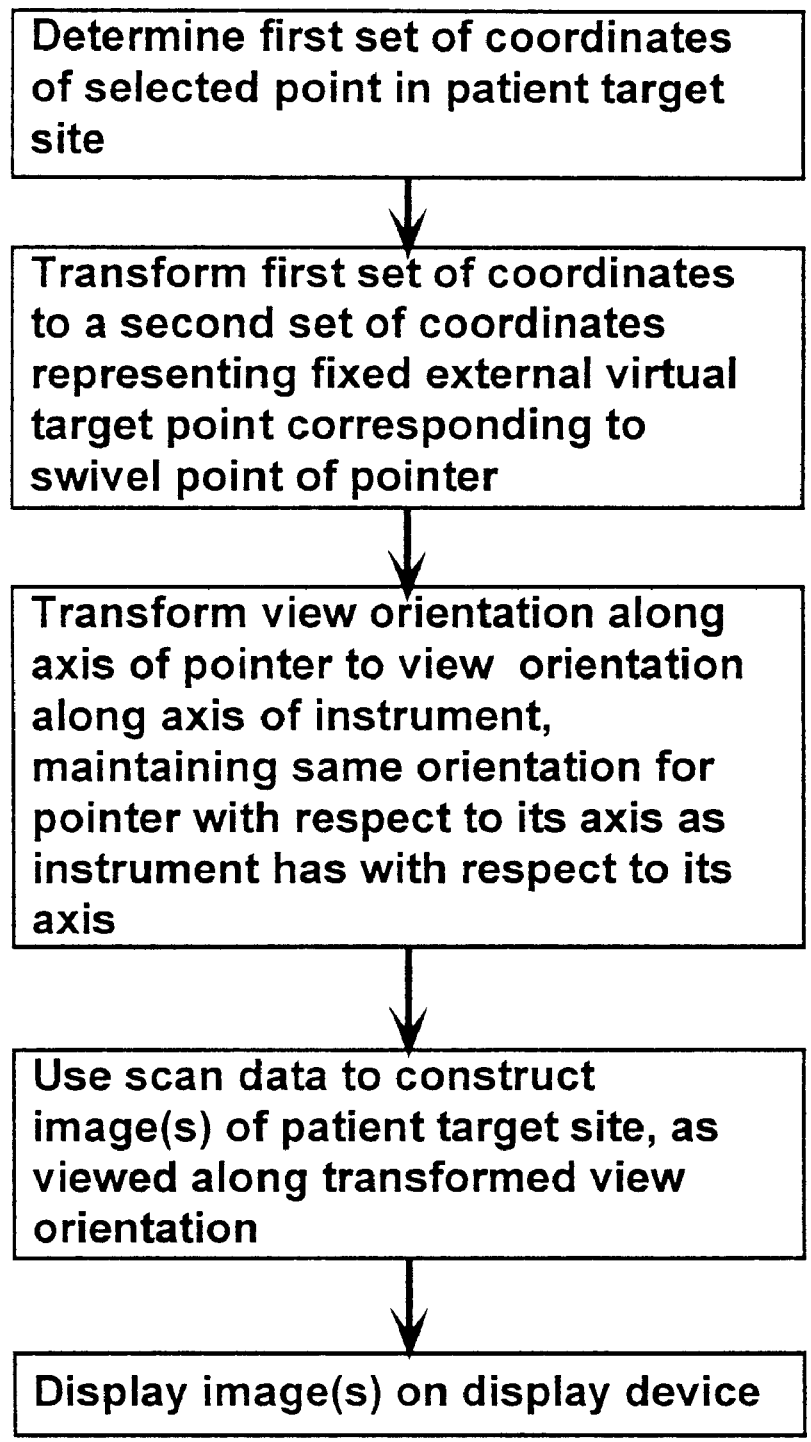
FIG. 8 is a flow chart illustrating a view orientation transformation in accordance with a third embodiment of the present invention.
Figure 9:
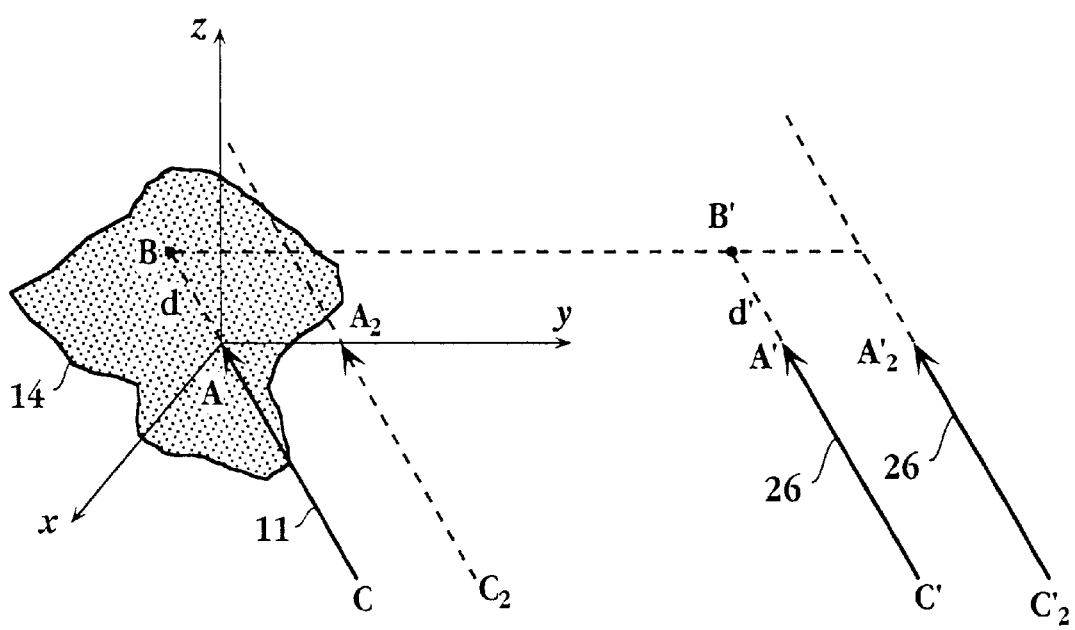
FIG. 9 is a schematic diagram illustrating the view transformation in accordance with the third embodiment of the present invention.

In another embodiment of the second mode of operation, a transformation is made between a view orientation along the axis of pointer 26 and a view orientation along the axis of instrument 11. Here, the view orientations are maintained along the axis of the instrument and the pointer respectively but not necessarily with respect to points B and B' when the pointer 26 is moved. An example of this embodiment is illustrated in FIGS. 8 and 9. This is merely one example of this embodiment; other variations are possible.

Referring now specifically to FIGS. 8 and 9, the user supplies input specifying a patient target site point B along the axis of instrument 11 a specified distance d from a known point, say A, on the instrument. The coordinates $x_1$, $y_1$, $z_1$ of the selected point B are determined with respect to a known point, say A, on the instrument.

Next, the user specifies an external virtual target point B' with respect to the axis of pointer 26, as previously described with regard to the first embodiment. The coordinates $x_1$, $y_1$, $z_1$ are transformed to a second set of coordinates $x_1$, $y_1$, $z_1$ representing B'.

A transformation is then made between the view orientation along the axis of pointer 26 and the view orientation along the axis of instrument 11. In this embodiment, the view orientations are maintained along the axis of the respective viewing device. Thus, if pointer 26 is moved laterally to the right, as shown in FIG. 9, the view orientation remains along the axis of the pointer, and corresponds to the view orientation along the axis of instrument 11, as if it had been moved laterally to the right the same distance, as shown in dashed line in FIG. 9. Similarly, if pointer 26 is rotated, with or without accompanying lateral motion, the view orientation remains along the axis of the pointer, and corresponds to the view orientation along the axis of instrument 11, as if it had been moved in the same manner.

Scan data is used to construct images of the patient target site 14, as viewed along the transformed view orientation, and these images are displayed on the display device.

As previously noted, various aspects of the image-guided surgery procedure, such as registration, tracking, image generation and navigation, may be implemented by a program of instructions (i.e., software). Various aspects of the present invention including transforming a target point in a patient target site to an external virtual target point and transforming the corresponding view orientations, which are part of the navigation step, may likewise be implemented by software. Software implementing one or more of the various aspects of the present invention may be written to run with existing software used for image-guided surgery.

The software for any or all of these tasks of the present invention may be fetched by the CPU from random-access memory (RAM) for execution. The software may be stored in read-only memory (ROM) on the computer system and transferred to RAM when in use. Alternatively, the software may be transferred to RAM or directly to the CPU for execution from ROM, or through a storage medium such as a disk drive or through an I/O device such as a modem. More broadly, the software may be conveyed by any medium that is readable by the CPU. Such media may include, for example, various magnetic media such as disks or tapes, various optical media such as compact disks, as well as various communication paths throughout the electromagnetic spectrum including infrared signals, signals transmitted through a network or the internet, and carrier waves encoded to transmit the software.

As an alternative to software implementation, the above-described aspects of the invention may be implemented with functionally equivalent hardware using discrete components, application specific integrated circuits (ASICs), digital signal processing circuits, or the like. Such hardware may be physically integrated with the computer processor(s) or may be a separate device which may be embodied on a computer card that can be inserted into an available card slot in the computer.

Thus, the above-described aspects of the invention can be implemented using software, hardware, or combination thereof. With that in mind, it is to be understood that the flow diagrams used to illustrate the various aspects of the present invention show the performance of certain specified functions and relationships therebetween. The boundaries of these functional blocks have been defined herein for convenience of description. Alternate boundaries may be defined so long as the appropriate functions are performed and the appropriate relationships therebetween are maintained. The diagrams and accompanying description provide the functional information one skilled in the art would require to implement a system to perform the functions required. Each of the functions depicted in the flow diagrams may be implemented, for example, by software, functionally equivalent hardware, or a combination thereof.

While embodiments of the invention have been described, it will be apparent to those skilled in the art in light of the foregoing description that many further alternatives, modifications and variations are possible. The invention described herein is intended to embrace all such alternatives, modifications and variations as may fall within the spirit and scope of the appended claims.

What is claimed:

1. Apparatus for use in an image-guided surgical or a diagnostic procedure at an internal target site of a patient, said apparatus comprising:
   (a) a data-storage medium for storing scan data representing internal scans of the patient target site;
   (b) an instrument defining a view axis, the instrument being adapted to be moved to a selected orientation with respect to the patient target site;
   (c) means for tracking the orientation of the instrument with respect to the patient target site as the instrument is moved;

(d) a display device; and
(e) a processor in communication with the data storage medium, the tracking means, and the display device, for carrying out steps (i)–(iii) in a first mode, and steps (iv)–(viii) in a second mode:
  (i) determining the orientation of the instrument view axis with respect to the patient target site, as the instrument is moved to a selected orientation with respect to the patient target site;
  (ii) using at least some of the scan data to construct an image of the patient target site, as viewed with respect to the orientation of the instrument;
  (iii) displaying the image on the display device;
  (iv) receiving input that indicates a selected orientation at which a virtual target point, external to the patient, is being viewed;
  (v) determining, from the input, the selected view orientation with respect to the virtual target point;
  (vi) transforming the view orientation determined in step (v) to a view orientation with respect to the selected patient target point;
  (vii) using the scan data to construct an image of the patient target site, as viewed along the transformed view orientation generated in step (vi); and
  (viii) displaying the image generated in step (vii) on the display device.

2. The apparatus of claim 1, wherein the tracking means is further operable to track the position of the instrument with respect to the patient target site and virtual target site, and the processor is further operable, in carrying out step (iv) to receive user input that indicates the selected orientation and position at which the virtual target point is being viewed, in carrying out step (v) to determine from the user input a view orientation and position with respect to the virtual target point, in-carrying out step (vi) to transform the view orientation and position with respect to the virtual target point to a view orientation and position, respectively, with respect to the selected patient target point, and in carrying out step (vii) to use the scan data to construct an image of the patient target site, as viewed along the transformed view orientation and position generated in step (vi).

3. The apparatus of claim 1, which further includes a user control for setting a reference condition for the first mode of processor operation, and the processor is operable to establish, as a reference orientation, the orientation of the medical instrument view axis determined in step (i) at the time the user sets the reference condition.

4. The apparatus of claim 3, wherein the processor is further operable to maintain the image displayed in step (iii) at the time the user sets the reference condition, and optionally, to display the image displayed in step (iii) and the image displayed in step (viii) simultaneously on the display device.

5. The apparatus of claim 1, which further includes a user input function by which the user can specify the coordinates of the virtual target point with respect to the medical instrument, and the processor is operable to maintain the specified virtual target-site coordinates with respect to the medical instrument, as the orientation of the instrument with respect to the virtual target point is selectively changed by the user.

6. The apparatus of claim 5, wherein the user input function is operable to specify target-site coordinates which are on the instrument view axis, a specified distance from a known point of the instrument.

7. The apparatus of claim 5, wherein the means for tracking the orientation of said instrument with respect to the patient includes (i) tracking elements carried on said instrument, (ii) positional elements adapted to be placed at fixed positions on the patient, and (iii) a sensing device for sensing the positions of the tracking and positional elements, and said sensing device is operably connected to said processor.

8. The apparatus of claim 1, which further includes a user input function by which the user can trigger the position of the virtual target point with respect to the medical instrument, at a selected position of the medical instrument, and the processor is operable to maintain the specified virtual target-site at a fixed position in space, as the orientation of the instrument with respect to the virtual target point is selectively changed by the user.

9. The apparatus of claim 8, wherein the user input function is further operable to trigger the positioning of the virtual target point on the instrument view axis, a specified distance from a known point of the instrument.

10. The apparatus of claim 8, wherein the means for tracking the orientation of said instrument with respect to the patient includes (i) tracking elements carried on said instrument, (ii) positional elements adapted to be placed at fixed positions on the patient, and (iii) a sensing device for sensing the positions of the tracking and positional elements, and the sensing device is operably connected to said processor.

11. The apparatus of claim 8, wherein the tracking means is further operable to track the position of said instrument with respect to the patient target site and the virtual target site, and the processor is further operable, in carrying out step (iv) to receive user input that indicates the a selected orientation and position at which the virtual target point is being viewed, in carrying out step (v) to determine from the user input, a view orientation and position with respect to the virtual target point, in carrying out step (vi) to transform the view orientation and position with respect to the virtual target point to a view orientation and position, respectively, with respect to the selected patient target point, and in carrying out step (vii) to use the scan data to construct an image of the patient's target site, as viewed along the transformed view orientation and position generated in step (vi).

12. The apparatus of claim 1, which further includes a positioning device having a pointer adapted to be moved about a fixed, virtual target point, and one or more position sensors operably connected to said processor for providing such user-determined input for step (v) of the processor operation.

13. The apparatus of claim 12, wherein the positioning device, includes a universal swivel adapted to be mounted adjacent and external to the patient, and having a swivel point corresponding to the virtual target point, an elongated pointer carried on the swivel for movement by the user to a selected orientation with respect to the virtual target point, and one or more position sensors for sensing the orientation and position of the pointer with respect to the virtual target point.

14. The apparatus of claim 12, which further includes a user control for setting a reference condition for the first mode of processor operation, and the processor is operable to establish, as a reference orientation, the orientation of the medical instrument view axis determined in step (i) at the time the user sets the reference condition.

15. The apparatus of claim 12, wherein the processor is operable, in carrying out steps (v) and (vi) to maintain the same orientation coordinates for the pointer, with respect to the virtual target point, as the medical instrument has with respect to the selected target point, such that the image displayed in step (viii) is from the same view orientation as that displayed in step (iii) when the medical instrument and the pointer have the same orientation in space.

16. The apparatus of claim 1, wherein the virtual target point is a fixed site defined by a physical structure adapted to be placed adjacent and external to the patient, and the user-determined input is supplied by a user-held pointer that can be moved to a selected position and orientation in space with respect to the virtual target point.

17. The apparatus of claim 16, wherein the user-held pointer is the medical instrument.

18. The apparatus of claim 17, wherein the means for tracking the position and orientation of the instrument with respect to the patient includes tracking elements carried on the instrument, positional elements adapted to be placed at fixed positions on the patient, and a sensing device for sensing the positions of the tracking and positional elements, and the sensing device is operably connected to the processor.

19. The apparatus of claim 18, wherein the physical structure defining the virtual target point also contains positional elements adapted to be sensed by the sensing device, and the processor is operable to determine the relative position and orientation of the medical instrument with respect to the virtual target point by input received from the sensing device.

20. The apparatus of claim 17, wherein the processor is operable to use input data about the position of the medical instrument with respect to the virtual target point, when the medical instrument is placed at a selected calibration position with respect to the virtual target point.

21. The apparatus of claim 16, wherein the processor is operable, in carrying out steps (iv) and (v) to shift the actual coordinates of the virtual target point so that they correspond to a point of the view axis of the medical instrument.

22. The apparatus of claim 16, wherein the pointer includes a three-dimensional position tracker adapted to be held by the user, and moved freely by the user to selected positions and orientation with respect to the virtual target point.

23. The apparatus of claim 22, wherein the pointer has a defined pointer axis, the processor is operable, in carrying out steps (iv) and (v) to shift the actual coordinates of the virtual target point so that they correspond to a point on the view axis of the pointer.

24. A device-readable medium embodying a program of instructions executable by the device for performing a method for use in an image-guided surgical or diagnostic procedure of transforming a view orientation, the program of instructions comprising instructions for:
  (a) storing scan data representing internal scans of a patient target site;
  (b) tracking the orientation of a medical instrument defining a view axis with respect to the patient target site, as the instrument is moved to a selected orientation with respect to the patient target site; and
  (c) carrying out the following steps (i)–(iii) in a first mode, and steps (iv)–(viii) in a second mode:
    (i) determining the orientation of the instrument view axis with respect to the patient target site, as the instrument is moved to a selected orientation with respect to the site;
    (ii) using at least some of the scan data to construct an image of the patient target site, as viewed with respect to the instrument;
    (iii) displaying the image on the display device;
    (iv) determining a view orientation with respect to a virtual target point external to the patient;
    (v) transforming the view orientation determined in step (iv) to a view orientation with respect to a selected patient target point;
    (vi) using the scan data to construct an image of the patient's target site, as viewed along the transformed view orientation generated in step (v); and
    (vii) displaying the image generated in step (vi) on the display device.

25. The device-readable medium of claim 24, wherein the tracking includes (i) placing tracking elements on the instrument and positional elements on the patient, and (ii) using a sensing device operably connected to the processor for sensing the positions of the tracking and positional elements.

26. The device-readable medium of claim 24, which further includes specifying the coordinates of the virtual target point with respect to the medical instrument, and the processor operates to maintain the specified virtual target-site coordinates with respect to the medical instrument, as the orientation of the instrument with respect to the virtual target point is selectively changed by the user.

27. The device-readable medium of claim 24, which further includes specifying the position of the virtual target point with respect to the medical instrument, at a selected position of the medical instrument, and the processor operates to maintain the specified virtual target-site at a fixed position in space, as the position orientation of the instrument with respect to the virtual target point is selectively changed by the user.

28. The device-readable medium of claim 24, wherein step (iv) is carried out by moving a pointer pivotally mounted on a universal swivel for movement to a selected orientation about a fixed, virtual target point, where the orientation of the pointer is detected by one or more position sensors operably connected to the processor.

29. The device-readable medium of claim 24, wherein step (iv) is carried out by moving a pointer about a fixed virtual target point defined by a physical structure positioned adjacent the patient.

30. The device-readable medium of claim 29, wherein the processor is operable to shift the actual coordinates of the virtual target point so that they correspond to a point of the view axis of the medical instrument.

31. The apparatus of claim 1, wherein the second mode of operation further includes transforming the coordinates of a selected point in the target site to the virtual target point.

32. The apparatus of claim 1, which further includes a positioning device in communication with the processor and adapted to moved about a fixed, virtual target point to select the orientation at which the virtual target point is being viewed.

33. The apparatus of claim 32, wherein the positioning device comprises a joystick or track ball.

* * * * *